United States Patent [19]

Elliott et al.

[11] Patent Number: 5,684,032
[45] Date of Patent: Nov. 4, 1997

[54] COMPOUNDS

[75] Inventors: John Duncan Elliott, Wayne; Jack Dale Leber, Doylestown; Scott Kevin Thompson, Phoenixville; Stacie Marie Halbert, Harleysville, all of Pa.

[73] Assignee: SmithKline Beecham Corporation, Philadelphia, Pa.

[21] Appl. No.: 539,451

[22] Filed: Oct. 5, 1995

Related U.S. Application Data

[63] Continuation-in-part of Ser. No. 355,354, Dec. 13, 1994, abandoned.

[51] Int. Cl.$^6$ .................................................. A61K 41/405
[52] U.S. Cl. ...................... 514/414; 514/419; 548/454; 548/491
[58] Field of Search ............................ 548/454, 491; 514/419, 414

[56] References Cited

U.S. PATENT DOCUMENTS

| | | | |
|---|---|---|---|
| 4,822,375 | 4/1989 | Lang et al. | 548/430 |
| 4,924,004 | 5/1990 | Ohlendorf et al. | 548/431 |
| 5,013,732 | 5/1991 | Bell et al. | 514/210 |

FOREIGN PATENT DOCUMENTS

WO94/14434   7/1994   WIPO.

OTHER PUBLICATIONS

Neber et al., Justus Liebigs Ann. Chem. vol. 471 (1929) p. 126 (pp. 113–145).

CA 121:205207m Indole–derivative . . . antagonists. Elliot et al., p. 1158, 1994.

*Primary Examiner*—Joseph McKane
*Attorney, Agent, or Firm*—Dara L. Dinner; Stephen Venetianer; Edward T. Lentz

[57] ABSTRACT

This invention relates to novel carboxylic acid indole compounds and compositions for use in the treatment of disease states mediated by the chemokine, Interleukin-8 (IL-8).

13 Claims, No Drawings

COMPOUNDS

RELATED U.S. APPLICATION DATA

This application is a continuation in part application of U.S. Ser. No. 08/355,354, filed 13 Dec. 1994, now abandoned.

FIELD OF THE INVENTION

This invention relates to a novel group of indole compounds, processes for the preparation thereof, the use thereof in treating IL-8 mediated diseases and pharmaceutical compositions for use in such therapy.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1 β or LPS, and by neutrophils themselves when exposed to LPS or chemotactic factors such as FMLP. M. Baggiolini et at, *J. Clin. Invest.* 84, 1045 (1989); J. Schroder et at, *J. Immunol.* 139, 3474 (1987) and *J. Immunol* 144, 2223 (1990); Strieter, et al, *Science* 243, 1467 (1989) and *J. Biol. Chem.* 264, 10621 (1989); Cassatella et al, *J. Immunol.* 148, 3216 (1992).

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8 promotes the accumulation and activation of neutrophils it has been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheimet et al, *Annu. Rev. Immunol.* 9, 617 (1991); Seitz et al., *J. Clin, Invest.* 87, 463 (1991); Miller et al., *Am. Rev. Respir. Dis.* 146, 427 (1992); Donnely et al., *Lancet* 341,643 (1993).

In vitro, IL-8 induces neutrophil shape change, chemotaxis, granule release, and respiratory burst, by binding to and activating receptors of the seven-transmembrane, G-protein-linked family, in particular by binding of IL-8 receptors. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil into the inflammatory site) would benefit by compounds which are inhibitors of IL-8 receptor binding.

SUMMARY OF THE INVENTION

This invention relates to the novel compounds of Formula (I) and pharmaceutical compositions comprising a compound of Formula (I) and a pharmaceutically acceptable diluent or carrier.

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present methods are represented by the structure

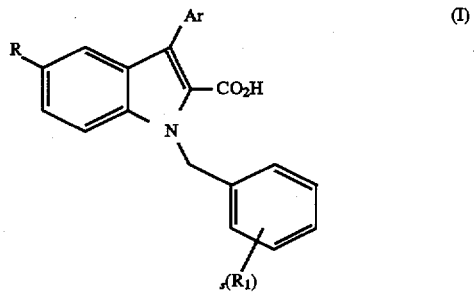

Ar is an optionally substituted phenyl or naphthyl group;

R is hydrogen, hydroxy, $C_{1-8}$ alkoxy, or $O-(CH_2)_n-R_6$;

$R_6$ is an optionally substituted $C_{3-7}$ cycloalkyl, optionally substituted $C_{3-7}$ cycloalkenyl, or an optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$ alkoxy, halosubstituted $C_{1-8}$ alkoxy, $-(CH_2)_s$ aryl, $O-(CH_2)_s$ aryl, $O-CH_2-O-C_{1-8}$ alkyl $O-(CH_2)_v, C(O)OC_{1-4}$ alkyl, $NO_2$, $S(O)mR_2$, $N(R_3)_2$, $NHC(O)R_4$, $-C(O)R_5$; or together two $R_1$ moieties may form a methylene dioxy ring system or together two $R_1$ moieties may form a 6 membered saturated or unsaturated ring system which may be optionally substituted;

s is an integer having a value of 1, 2, or 3;

v is an integer having a value of 1, 2, 3, or 4;

m is 0 or an integer having a value of 1 or 2;

t is 0 or an integer having a value of 1, 2; 3 or 4;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl; $R_5$ is hydrogen, optionally substituted $C_{1-8}$ alkyl, or $C_{1-8}$ alkoxy;

or pharmaceutically acceptable salts thereof.

DETAILED DESCRIPTION OF THE INVENTION

The novel compounds of Formula (I) may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

Novel compounds of Formula (I) are represented by the structure

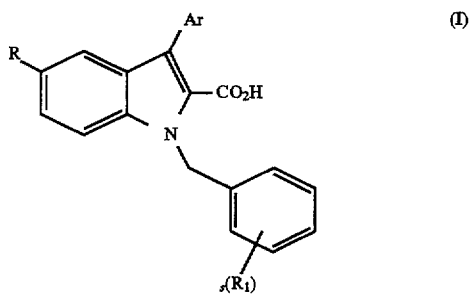

wherein

Ar is an optionally substituted phenyl or naphthyl group;

R is hydrogen, hydroxy, $C_{1-8}$ alkoxy, or $O—(CR_8R_9)_n—R_6$;

$R_6$ is an optionally substituted $C_{3-7}$ cycloalkyl, optionally substituted $C_{3-7}$ cycloalkenyl, or optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, $O—CH_2—O—C_{1-8}$alkyl, $—(CH_2)_t$ aryl, $O—(CH_2)_t$ aryl, $—O—(CH_2)_v C(O)OC_{1-4}$alkyl, $NO_2$, $S(O)_m R_2$, $N(R_3)_2$, $NHC(O)R_4$, $—C(O)R_5$, or together two $R_1$ moieties may form a methylene dioxy ring system, or together two $R_1$ moieties may form a 6 membered saturated or unsaturated ring system which may be optionally substituted;

t is 0 or an integer having a value of 1, 2, 3, or 4;

v is an integer having a value of 1, 2, 3, or 4;

s is an integer having a value of 1, 2, or 3;

m is 0 or an integer having a value of 1 or 2;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl;

$R_5$ is hydrogen, optionally substituted $C_{1-8}$ alkyl, or $C_{1-8}$ alkoxy;

$R_8$ and $R_9$ are independently hydrogen or $C_{1-4}$ alkyl; provided that a) when R is hydrogen, and Ar is 4-methoxyphenyl, then $R_1$ is not a (2-chloro-4,5-methylenedioxy), or a (4,5-methylenedioxy);

b) when R is hydrogen, and Ar is 2-nitrophenyl, then $R_1$ is not hydrogen;

c) when R is hydrogen, and Ar is 2-hydroxymethyl-4-methoxyphenyl, then $R_1$ is not (2-chloro-4,5-methylenedioxy);

or pharmaceutically acceptable salts thereof.

Ar is optionally substituted phenyl or naphthyl group. Preferably Ar is an unsubstituted naphthyl or an optionally substituted phenyl. The aryl ring may be substituted independently one or more times, suitably one to three times, by halogen, such a chlorine or fluorine; $C_{1-8}$ alkyl, such as methyl; halosubstituted $C_{1-8}$ alkyl, such as $CF_3$; optionally substituted $—(CH_2)_n$ aryl, such as phenyl; hydroxy; halosubstituted $C_{1-8}$ alkoxy, such as $—OCF_3$; $C_{1-8}$ alkoxy, such as methoxy; optionally substituted $O—(CH_2)_n$ aryl, such as phenoxy or benzyloxy; $NO_2$; $N(R_3)_2$, amines and substituted amines, such as in $N(R_3)_2$ wherein the $R_3$ moieties are independently hydrogen, or $C_{1-4}$ alkyl, or together with the nitrogen to which they are attached form a 5 to 7 membered saturated or unsaturated ring, such as pyrrole, piperidine, or pyridine; or $—C(O)R_5$, wherein $R_5$ is hydrogen, optionally substituted $C_{1-8}$ alkyl, or $C_{1-8}$ alkoxy; and wherein n is 0, or an integer having a value of 1 to 4. Suitably, the substituents are not 2,4-di-methoxy; or 3,5-diCF$_3$.

More preferably the substituents are chlorine, fluorine, methyl, $OCF_3$, $CF_3$, amine, $C(O)H$, phenyl, methoxy, phenoxy, or phenyl. More specifically the substituents are chloro, such as 4-fluoro, 4-chloro; di-chloro, such as 2,4-dichloro, 3,5-dichloro, or 3-chloro-4-fluoro; $CF_3$, such as 4-$CF_3$; methoxy, such as 4-methoxy; phenoxy, such as 4-phenoxy; phenyl such as 4-phenyl; alkyl such as 4-methyl; amino such as 3-amino; or $C(O)R_5$, such as 2-$C(O)H$ or 4-$C(O)H$.

R is hydrogen, hydroxy, $C_{1-8}$ alkoxy, or $O—(CR_8R_9)_n—R_6$. $R_6$ is an optionally substituted $C_{3-7}$ cycloalkyl, optionally substituted $C_{3-7}$ cycloalkenyl, or an optionally substituted aryl. Preferably R is $C_{1-8}$ alkoxy or an optionally substituted $O—(CR_8R_9)_n$-aryl, wherein the aryl is phenyl, such as in a benzyloxy group.

When R is an optionally substituted $O—(CR_8R_9)_n—R_6$ group, the $R_6$ ring may be optionally substituted one or more times independently by halogen; hydroxy; hydroxy substituted $C_{1-10}$alkyl; $C_{1-10}$ alkyl, such as methyl, ethyl, propyl, isopropyl, or t-butyl; halosubstituted $C_{1-10}$ alkyl, such $CF_3$; $C_{1-10}$ alkoxy, such as methoxy, ethoxy, isopropyloxy, or propyloxy; optionally substituted $C_{1-10}$ alkoxy, such as methoxymethoxy or trifluoromethoxy; $S—C_{1-10}$ alkyl, such as methyl thio; amino, mono & di-substituted amino, such as in the $N(R_3)_2$ group; $N(R_3)—C(O)C_{1-10}$alkyl, such as acetamido; $C(O)C_{1-10}$alkyl such as 2,2-dimethylpropanoyl; cyano, nitro; a methylene dioxy ring system; an optionally substituted aryl, such as phenyl, or an optionally substituted arylalkyl, such as benzyl or phenethyl, wherein these aryl moieties may be substituted one to two times by halogen; hydroxy; hydroxy substituted alkyl; $C_{1-10}$ alkoxy; $S(O)_m C_{1-10}$ alkyl, wherein m is 0, 1 or 2; amino, mono & di-substituted amino, such as in the $N(R_3)_2$ group; $C_{1-10}$ alkyl, or halosubstituted $C_{1-10}$ alkyl, such as $CF_3$. Suitably, when two substituents form a methylene dioxy ring system it is preferably when $R_6$ is an aryl group, more preferably a phenyl ring.

Suitably when $R_6$ is a $C_{3-7}$ cycloalkyl moiety it is preferably a cyclohexyl ring, such as in cyclohexylmethoxy.

$R_1$ is hydrogen, halogen, halosubstituted $C_{1-8}$ alkyl, $C_{1-8}$ alkyl, hydroxy, $C_{1-8}$alkoxy, halosubstituted $C_{1-8}$ alkoxy, $O—CH_2—O—C_{1-8}$alkyl, $—(CH_2)_t$aryl, $O—(CH_2)_t$ aryl, $—O—(CH_2)_v C(O)OC_{1-4}$alkyl, $NO_2$, $S(O)_m R_2$, $N(R_3)_2$, $NHC(O)R_4$, or $—C(O)R_5$; or together two $R_1$ moieties may form a methylenedioxy ring system; or together two $R_1$ moieties may form a 6 membered saturated or unsaturated ring system which may be optionally substituted; and t is 0 or an integer having a value of 1 to 4.

Preferably when the phenyl ring is monosubstituted, the $R_1$ group is in the 4-position. When the phenyl ring is substituted by a methylenedioxy group it is preferably in the 3,4-position; and more preferably the phenyl ring may also be additionally substituted by another $R_1$, such as halogen, preferably fluorine or chlorine. When the two $R_1$ moieties form a 6 membered saturated or unsaturated ring system, which may contain 0 to 2 double bonds, and is preferably an aromatic ring forming a naphthyl ring system, which ring may be optionally substituted as defined herein. Preferred substituents for $R_1$ are $NO_2$, $OCF_3$, $OCH_3$, $CH_3$, benzyloxy, phenoxy, hydrogen or halogen, preferably fluorine or chlorine, more preferably chlorine.

$R_2$ is an optionally substituted $C_{1-8}$ alkyl; and $R_4$ is independently hydrogen, or $C_{1-4}$ alkyl.

$R_3$ is independently hydrogen, or $C_{1-4}$ alkyl, or together with the nitrogen to which they are attached form a 5 to 7 membered saturated or unsaturated ring; such as such as pyrrole, piperidine, or pyridine.

Exemplified Compounds of Formula (I) include:
Exemplified compounds of Formula (I) include:
1-(2-chloro-4,5-methylenedioxyphenylmethyl)-3-(4-methoxyphenyl)indole-2-carboxylic acid;
1-(2-chloro-4,5-methylenedioxyphenylmethyl)-3-phenyl-5-phenylmethylindole-2-carboxylic acid;
1-(2-chloro-4,5-methylenedioxyphenylmethyl)-3-phenylindole-2-carboxylic acid;
1-(2-chloro-4,5-methylenedioxyphenylmethyl)-3-(1-naphthyl)indole-2-carboxylic acid;
1-(2-chloro-4,5-methylenedioxyphenylmethyl)-3-(3,5-dichlorophenyl)indole-2-carboxylic acid;
1-(2-chloro-4,5-methylenedioxyphenylmethyl)-3-(3-chloro-4-fluorophenyl)indole-2-carboxylic acid;
1-(2-Chloro-4,5-methylenedioxybenzyl)-3-phenyl-5-propyloxyindole-2-carboxylic acid
1-(2-Chloro-4,5-methylenedioxybenzyl)-3-phenyl-5-isopropyloxyindole-2-carboxylic acid
1-(2-Chloro-4,5-methylenedioxybenzyl)-3-phenyl-5-(4-trifluoromethylbenzyloxy)-indole-2-carboxylic acid
1-(2-Chloro-4,5-methylenedioxybenzyl)-3-phenyl-5-(3-trifluoromethylbenzyloxy)-indole-2-carboxylic acid
1-(2-Chloro-4,5-methylenedioxybenzyl)-5-(3,4-methylenedioxybenzyloxy)-3-phenylindole-2-carboxylic acid
1-(2-Chloro-4,5-methylenedioxybenzyl)-5-(4-methoxybenzyloxy)-3-phenylindole-2-carboxylic acid
1-(2-Chloro-4,5-methylenedioxybenzyl)-5-cyclohexylmethoxy-3-phenylindole-2-carboxylic acid
1-(2-Chloro-4,5-methylenedioxybenzyl)-3-phenyl-5-(2-trifluoromethylbenzyloxy)-indole-2-carboxylic acid
1-(2-Chloro-4,5-methylenedioxybenzyl)-3-(4-methylphenyl)-5-(4-methylthiobenzyloxy)indole-2-carboxylic acid
1-(2-Chloro-4,5-methylenedioxybenzyl)-3-(3,5-dichlorophenyl)-5-(4-trifluoromethoxybenzyloxy)indole-2-carboxylic acid
1-(2-Chloro-4,5-methylenedioxybenzyl)-5-(2-chloro-4,5-methylenedioxybenzyloxy)-3-(3,5-dichlorophenyl) indole-2-carboxylic acid
1-(2-Chloro-4,5-methylenedioxybenzyl)-5-(3-furylmethoxy)-3-(4-methylphenyl)-indole-2-carboxylic acid
1-(2-Chloro-4,5-methylenedioxybenzyl)-5-(4-tert-butylbenzyloxy)-3-phenylindole-2-carboxylic acid
1-(2-Chloro-4,5-methylenedioxybenzyl)-5-(3-methoxybenzyloxy)-3-phenylindole-2-carboxylic acid
1-(2-Chloro-4,5-methylenedioxybenzyl)-5-[4-(2,2-dimethylpropanoyl)benzyloxy]-3-phenylindole-2-carboxylic acid
1-(2-Chloro-4,5-methylenedioxybenzyl)-5-(2-methoxybenzyloxy)-3-phenylindole-2-carboxylic acid
1-(2-Chloro-4,5-methylenedioxybenzyl)-5-(4-cyanobutylbenzyloxy)-3-phenylindole-2-carboxylic acid
1-(2-Chloro-4,5-methylenedioxybenzyl)-5-(2-chloro-4,5-methylenedioxybenzyloxy)-3-phenylindole-2-carboxylic acid
1-(2-Chloro-4,5-methylenedioxybenzyl)-5-(4-methylthiobenzyloxy)-3-phenylindole-2-carboxylic acid
5-Benzyloxy-1-(2-chloro-4,5-methylenedioxybenzyl)-3-(4-formylphenyl)-2-carboxylic acid
5-Benzyloxy-1-(2-chloro-4,5-methylenedioxybenzyl)-3-(2-formylphenyl)-2-carboxylic acid
5-Benzyloxy-1-(2-chloro-4,5-methylenedioxybenzyl)-3-(4-fluorophenyl)indole-2-carboxylic acid
3-(3-Aminophenyl)-5-benzyloxy-1-(2-chloro-4,5-methylenedioxybenzyl)indole-2-carboxylic acid
5-Benzyloxy-1-(2-chloro-4,5-methylenedioxybenzyl)-3-(2,4-dichlorophenyl)indole-2-carboxylic acid.

A preferred salt form of the compounds of Formula (I) is the sodium salt.

A preferred subgroup of compounds within Formula (I) are represented by the structure having the formula:

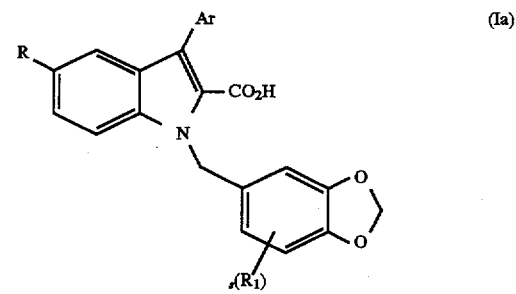

wherein

Ar is an optionally substituted phenyl or naphthyl group;

R is hydrogen, hydroxy, $C_{1-8}$ alkoxy, or optionally substituted O—$(CH_2)_n$phenyl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$alkoxy, halosubstituted $C_{1-8}$ alkoxy, aryl, aryl $C_{1-4}$ alkyl, aryloxy, aryl$C_{1-4}$alkyloxy, $NO_2$, or $N(R_3)_2$;

s is an integer having a value of 1, 2 or 3;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl; provided that when R is hydrogen, and Ar is 4-methoxyphenyl, then $R_1$ is not a (4-chloro-1,3-benzodioxol-5-yl) methyl, a (6-chloro-1,3-benzodioxol-5-yl)methyl or a (1,3-benzodioxol-5-yl)methyl;

or pharmaceutically acceptable salts thereof.

Specifically exemplified compounds of Formula (Ia) wherein $R_1$ is additionally a chlorine, are shown in the table illustrated below.

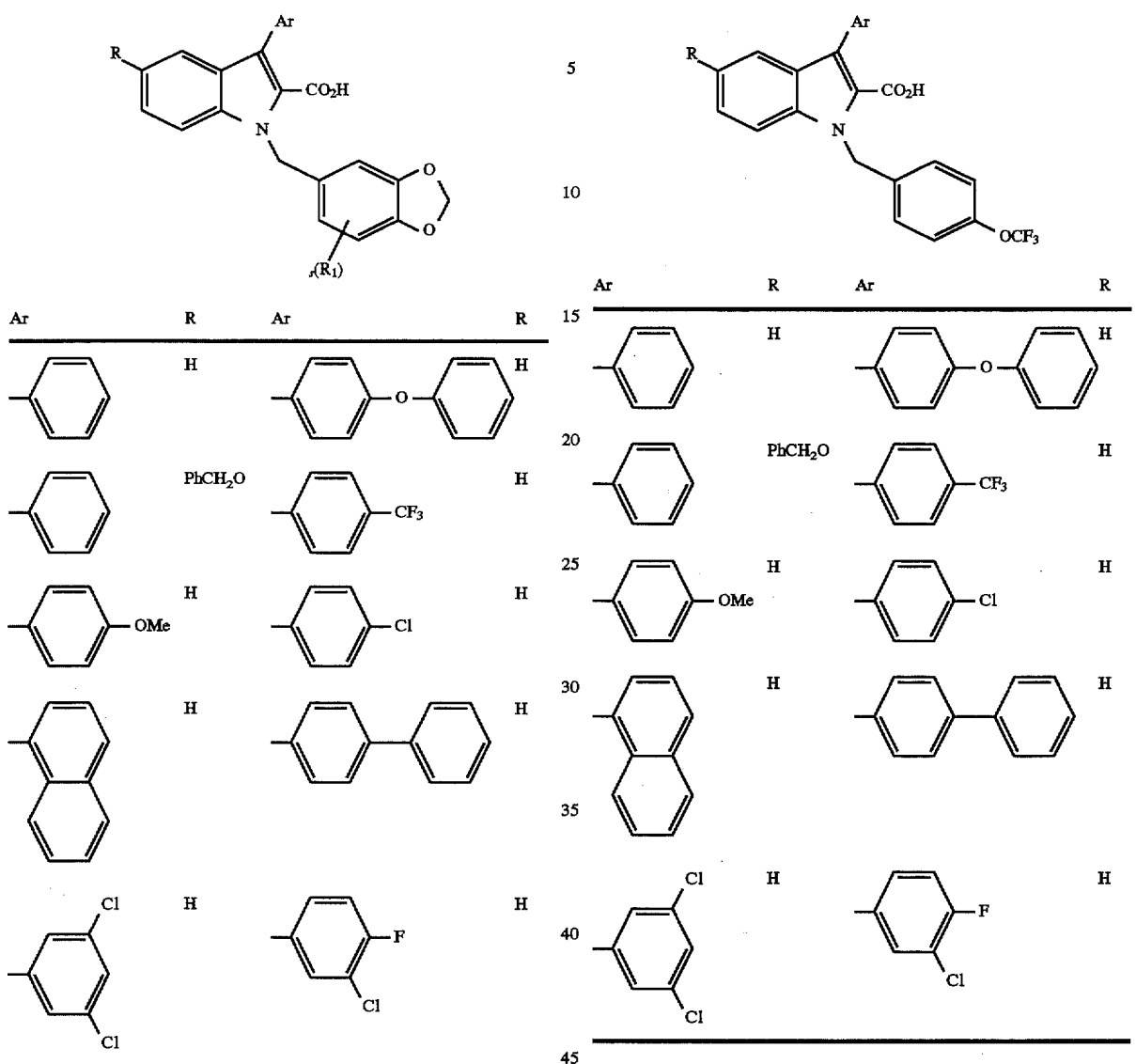

Another aspect of the present invention is the preferred subgroup of compounds within Formula (I) are represented by the structure having the formula:

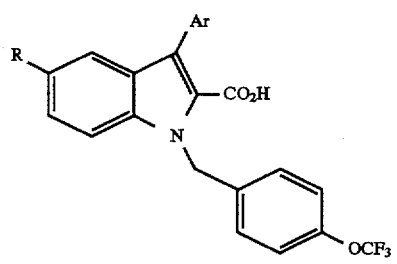

(Ib)

wherein R, $R_1$ and Ar are as defined for Formula (I).

Additional exemplified compounds of Formula (I) include:

Another aspect of the present invention is the preferred subgroup of compounds within Formula (I) are represented by the structure having the formula (Ic):

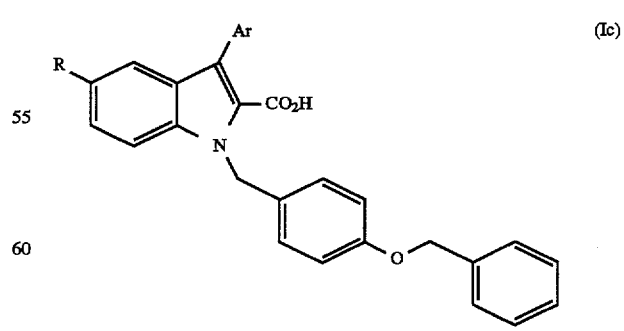

(Ic)

Specifically exemplified compounds of Formula (Ic) include:

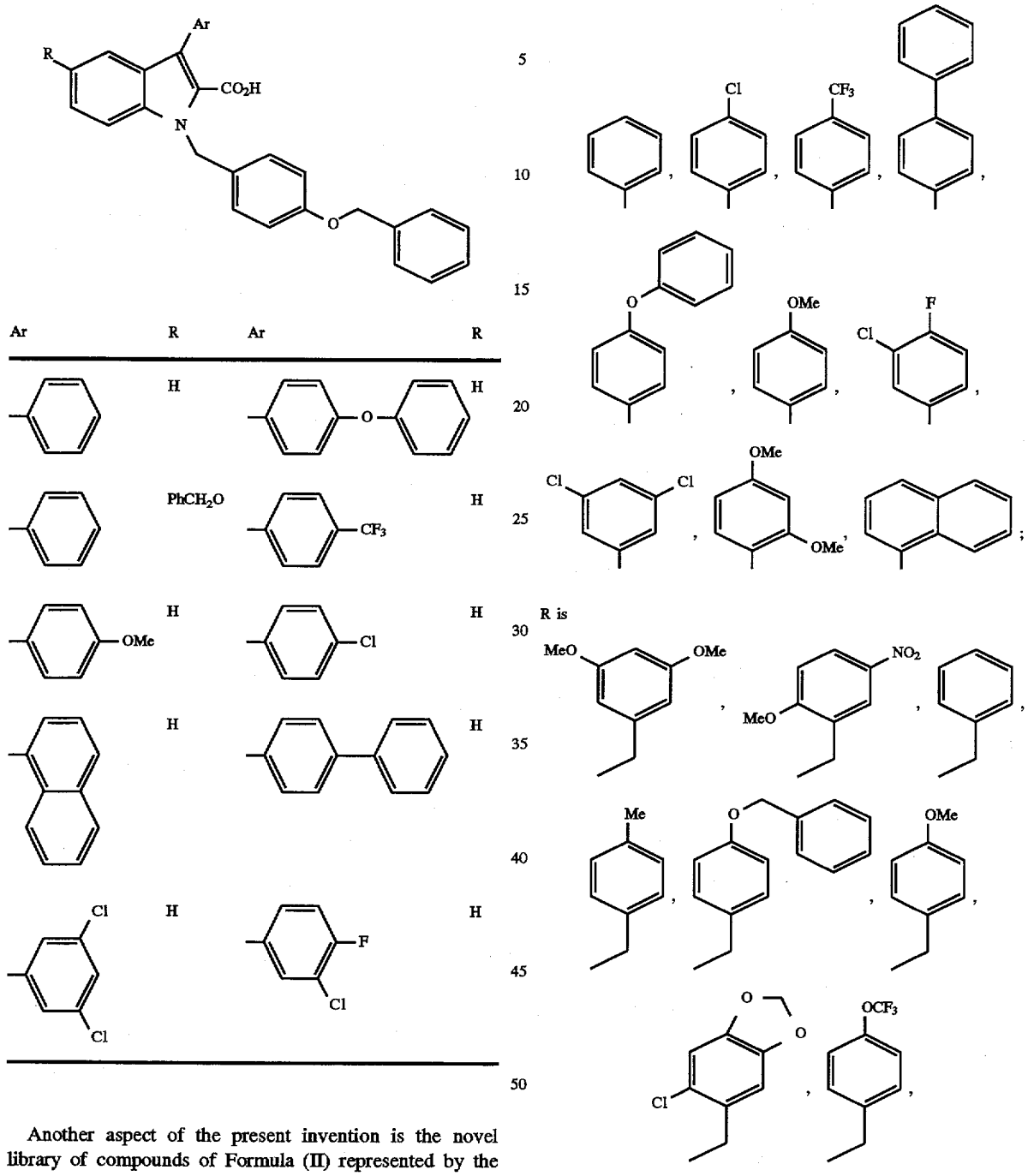

Another aspect of the present invention is the novel library of compounds of Formula (II) represented by the structure:

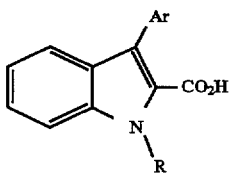
(II)

wherein Ar is

[structures shown]

For purposes herein, there are 8 defined sublibraries of compounds of Formula (II) as determined by fixing the R group and varying the 10 Ar groups, each designated by the formula (IIa) through (IIh). Each of these sublibraries have individually been found to inhibit IL-8 by the assays as taught herein.

The library of compounds of Formula (II) are useful for binding to G-protein coupled receptors. G-protein coupled receptors, well known in the literature, are a 7-transmembrane receptor which uses G-proteins as part of their signaling mechanism, including but not limited to IL-8 receptors, dopamine receptors muscarinic acetylcholine receptors and the like.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m $C_{1-10}$ alkyl, wherein m is 0, 1 or 2, such as methyl thio, methylsulfinyl or methyl sulfonyl; amino, mono & di-substituted amino, such as in the $N(R_3)_2$ group; $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, wherein these aryl moieties may be substituted one to two times by halogen; hydroxy; hydroxy substituted alkyl; $C_{1-10}$ alkoxy; $S(O)_m$ $C_{1-10}$ alkyl; amino, mono & di-substituted amino, such as in the $N(R_3)_2$ group; $C_{1-10}$ alkyl, or halosubstituted $C_{1-10}$ alkyl, such as $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 3 to 8 carbons, having one or more bonds which are unsaturated, including but not limited to cyclopentenyl, or cyclohexenyl.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl ring.

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-8}$ alkyl as defined above attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized S $(O)_2$ moiety.

The compounds of Formula (I) may be obtained by applying synthetic procedures, some of which are illustrated in the Schemes below. The synthesis provided for in these Schemes is applicable for the producing compounds of Formula (I) having a variety of different R, $R_1$, and Ar groups which are reacted, employing optional substituents which are suitably protected, to achieve compatibility with the reactions outlined herein. Subsequent deprotection, in those cases, then affords compounds of the nature generally disclosed. Once the indole nucleus has been established, further compounds of Formula (I) may be prepared by applying standard techniques for functional group interconversion, well known in the art.

Compounds of the formula I wherein $R^1$=H and $R^3$=2-chloro-4,5-methylenedioxyphenylmethyl are prepared by methods analogous to those described in Scheme 1, below.

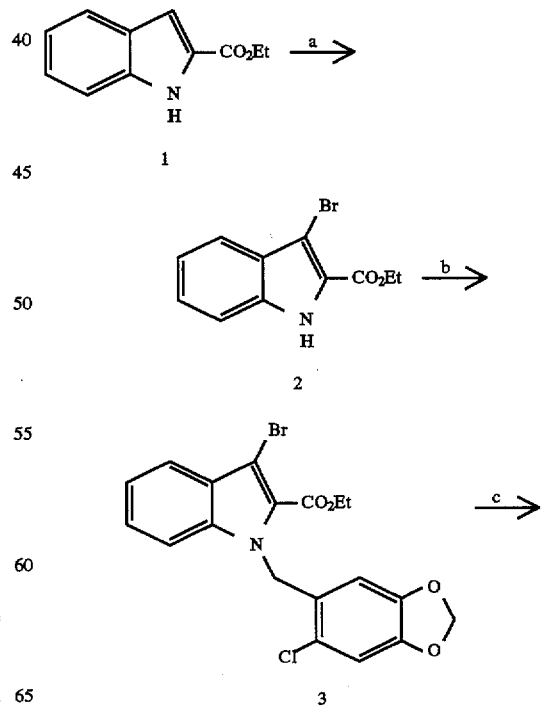

Scheme 1

-continued
Scheme 1

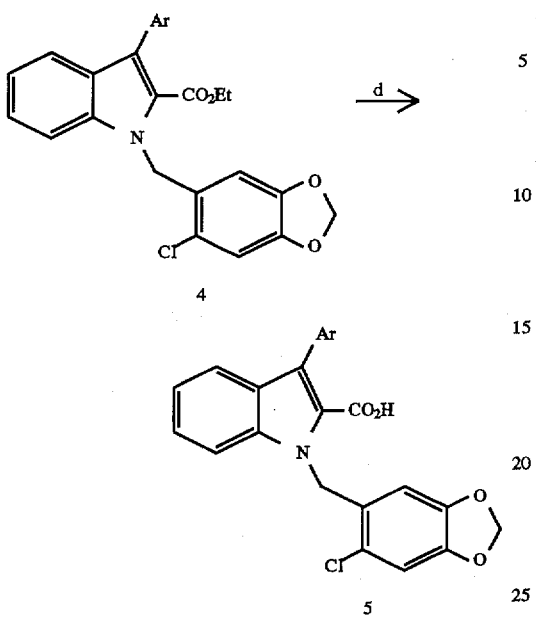

a) Br₂, DMF;
b) NaH, DMF, 6-chloropiperonyl chloride;
c) ArB(OH)₂, Pd(PPh₃)₄, Na₂CO₃, PhMe, EtOH, H₂O;
d) KOH, THF, EtOH, H₂O 1-Scheme 1 is treated with bromine in DMF at room temperature to provide 2-Scheme 1. This material is alkylated by treatment with a strong base (such as sodium hydride or potassium hydride) in an aprotic solvent (such as DMF or THF) and 6-chloropiperonyl chloride. 3-Scheme 1 is arylated by treatment with a palladium (0) catalyst (such as Pd(PPh₃)₄, ArPd(PPh₃)₂I, Pd(OAc)₂, [(allyl)PdCl]₂ or Pd₂(dba)₃), an arylboronic acid (such as phenylboronic acid, 4-methoxyphenylboronic acid, 2,4-dimethoxyphenylboronic acid, 3,5-dichlorophenylboronic acid, 3-chloro-4-fluorophenylboronic acid or 1-naphthylboronic acid) and a base (such as sodium carbonate, potassium carbonate, potassium phosphate, lithium hydroxide, sodium hydroxide, potassium hydroxide or thallium hydroxide) in a mixture of toluene, ethanol and water. A mixture of acetonitrile and water or DME and water may be substituted for this solvent mixture. The arylated product, 4-Scheme 1, is alkylated by treatment with a hydroxide base (such as potassium hydroxide, sodium hydroxide or lithium hydroxide) to yield carboxylic acid 5-Scheme 1.

In an alternative manner, compounds of the formula I wherein R²=phenyl are prepared by methods analogous to those described in Scheme 2. 1-Scheme 2 is treated with bromine in DMF at room temperature to provide 2-Scheme 2. This material is arylated by treatment with a palladium (0) catalyst (such as Pd(PPh₃)₄, ArPd(PPh₃)₂I, Pd(OAc)₂, [(allyl)PdCl]₂ or Pd₂(dba)₃), phenylboronic acid and a base (such as sodium carbonate, potassium carbonate, potassium phosphate, lithium hydroxide, sodium hydroxide, potassium hydroxide or thallium hydroxide) in a mixture of toluene, ethanol and water. A mixture of acetonitrile and water or DME and water may be substituted for this solvent mixture. The arylated product, 3-Scheme 2, is alkylated by treatment with a strong base (such as sodium hydride or potassium hydride) in an aprotic solvent (such as DMF or THF) and an alkyl halide (such as 6-chloropiperonyl chloride or 4-benzyloxybenzyl chloride). 4-Scheme 2 is saponified by treatment with a hydroxide base (such as potassium hydroxide, sodium hydroxide or lithium hydroxide) to yield carboxylic acid 5-Scheme 2.

Scheme 2

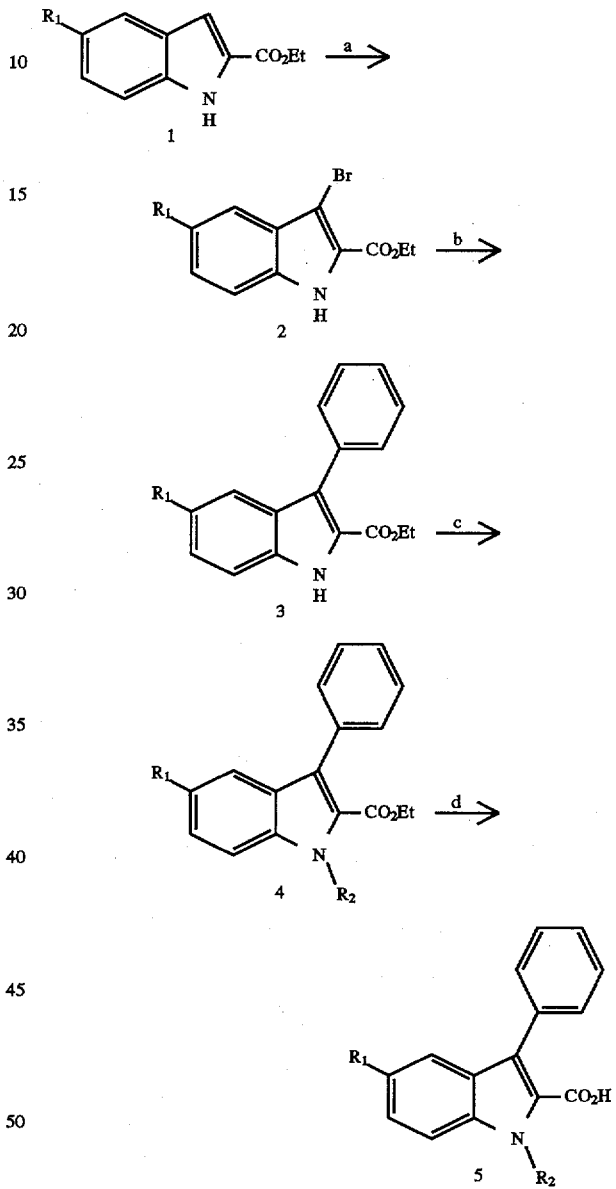

a) Br₂, DMF;
b) PhB(OH)₂, Pd(PPh₃)₄, Na₂CO₃, PhMe, EtOH, H₂O;
c) NaH, DMF, R₂—Cl;
d) K THF, EtOH, H₂O

Compounds of the formula I wherein R¹ is other than OCH₂Ph are prepared by methods analogous to those described in Scheme 3. Treatment of 1-Scheme 3 with a suitable hydrogenation catalyst (such as palladium on carbon) under a hydrogen atmosphere in a polar solvent (such as ethyl acetate or ethanol) should provide 2-Scheme 3. This material may be alkylated by treatment with a strong base (such as sodium hydride or potassium hydride) in an aprotic solvent (such as DMF or THF) and an alkyl halide. Alternatively, 3-Scheme 3 may be prepared by treatment with a primary or secondary alcohol, triphenylphosphine and an azodicarboxylic ester (such as diethyl azodicarboxylate or diisopropylazodicarboxylate) in an aprotic solvent) such as THF or N-methylmorpholine). 3-Scheme 3 may be saponified by treatment with a hydroxide base (such as potassium hydroxide, sodium hydroxide or lithium hydroxide) to yield carboxylic acid 4-Scheme 3.

Scheme 3

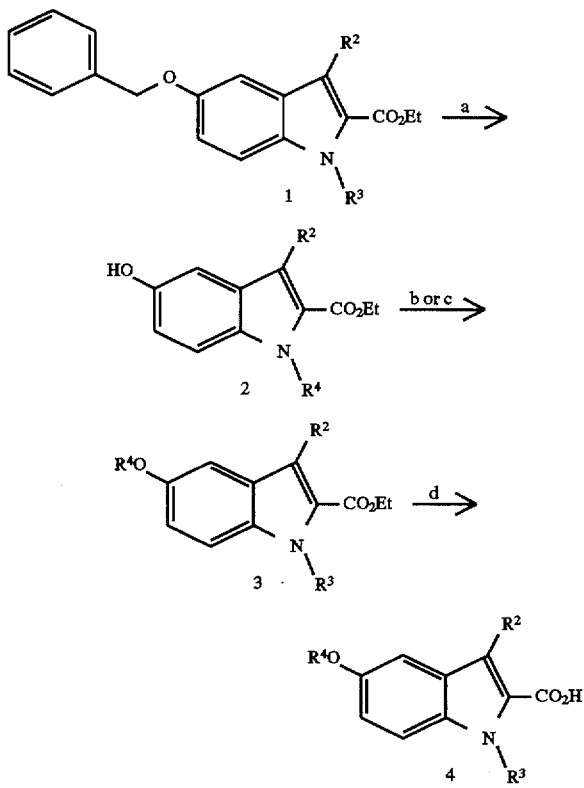

a) $H_2$, Pd—C, EtOAc;
b) NaH, DMF, $R^4$—Cl or $R^4$—Br;
c) $R^4$OH, $PPh_3$, DEAD, THF
d) KOH, THF, EtOH, $H_2O$

The library of compounds of Formula (II) may be obtained by applying synthetic procedures analogous to those as described in the scheme, Scheme 4, below.

Scheme 4

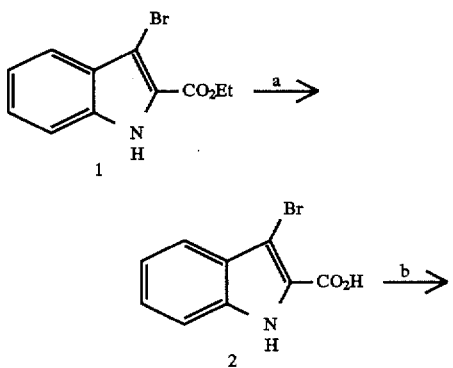

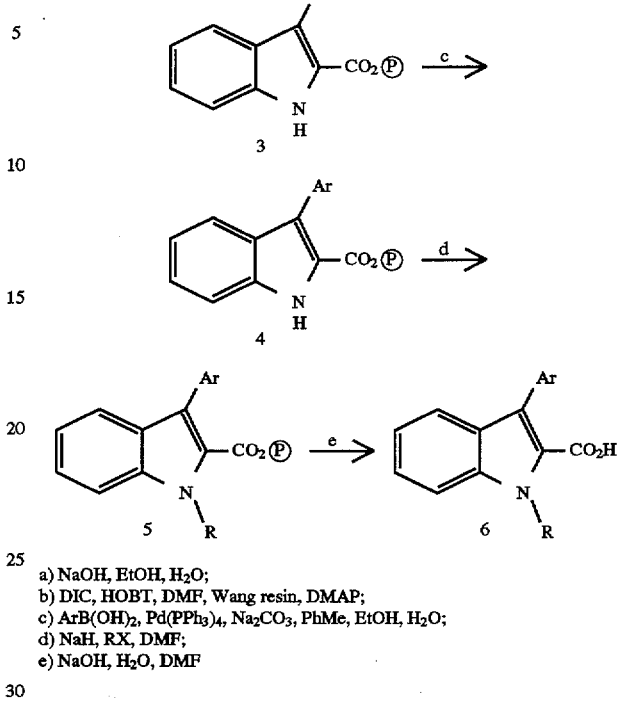

a) NaOH, EtOH, $H_2O$;
b) DIC, HOBT, DMF, Wang resin, DMAP;
c) $ArB(OH)_2$, $Pd(PPh_3)_4$, $Na_2CO_3$, PhMe, EtOH, $H_2O$;
d) NaH, RX, DMF;
e) NaOH, $H_2O$, DMF 1-Scheme4 is saponified by treatment with an alkali metal hydroxide (such as potassium hydroxide, sodium hydroxide or lithium hydroxide) to yield carboxylic acid 2-Scheme4. This material is coupled to a suitable resin, designated by the P in a circle, in the instance, shown it is a Wang resin, by activation of compound 2-Scheme4 (for example by treatment with diisopropylcarbodiimide and 1-hydroxybenzotriazole in DMF) then stirring with the resin in an aprotic solvent such as DMF and a base such as 4-dimethylaminopyridine. This material is arylated by a method analogous to those described for compound 4-Scheme 1. The arlyated compound 4-Scheme4 is alkylated by a method analogous to those described for compound 3-Scheme 1. The alkylated product 5-Scheme4 is released from the resin by treatment with an aqueous alkali metal hydroxide (such as potassium hydroxide, sodium hydroxide or lithium hydroxide) in an appropriate solvent such as DMF to afford, after acidification, the carboxylic acid 6-Scheme4.

Pharmaceutically acid addition salts of compounds of Formula (I) may be obtained in known manner, for example by treatment thereof with an appropriate amount of acid in the presence of a suitable solvent.

In the Examples, all temperatures are in degrees Centigrade (°C.). Mass spectra were performed upon a VG Zab mass spectrometer using fast atom bombardment, unless otherwise indicated. $^1$H-NMR (hereinafter "NMR") spectra were recorded at 250 MHz or 400 MHz using a Bruker AM 250 or Am 400 spectrometer, respectively. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anydrous conditions in an argon atmosphere unless otherwise indicated.

Example 1

Preparation of 5-benzyloxy-1-(2-chloro-4,5-methylenedioxybenzyl)-3-phenylindole-2-carboxylic acid a) ethyl 5-benzyloxy-3-bromoindole-2-carboxylate To a suspension of ethyl 5-benzyloxyindole-2-carboxylate (21.9 g, 74.0 mmol) in DMF (30 mL) was added dropwise over 10 min a solution of bromine (11.83 g, 74.0 mmol, 3.8 mL) in DMF (40 mL). After stirring an additional 20 min at room temperature, the solution was partitioned between 3 N HCl and ethyl acetate. The organic layer was washed sequentially with water, saturated aqueous sodium bicarbonate, water and saturated brine, then dried (MgSO$_4$), filtered and concentrated to leave a white solid. The solid was recrystallized from ethyl acetate to provide the title compound (19.6 g, 71%). $^1$H NMR (400 MHz, CDCl$_3$) δ 8.96 (br s, 1H), 7.52–7.30 (m, 6H), 7.15–7.10 (m, 2H), 5.14 (s, 2H), 4.46 (q, J=7.1 Hz, 2H), 1.46 (t, J=7.1 Hz, 3H).

b) ethyl 5-benzyloxy-3-phenylindole-2-carboxylate

The compound of Example 1(a) (2.28 g, 6.1 mmol), phenylboronic acid (0.97 g, 7.9 mmol) and tetrakis(triphenylphosphine)palladium(0) (141 mg, 0.12 mmol) were combined and to the mixture was added toluene (20 mL), ethanol (20 mL) and 2 N sodium carbonate (8 mL). The mixture was heated with stirring at 90° C. for 17 h, then partitioned between 3 N HCl and ethyl acetate. The organic layer was washed sequentially with water, saturated aqueous sodium bicarbonate and saturated brine, then dried (MgSO$_4$), filtered and concentrated to leave a pale yellow solid. The solid was recrystallized from ethanol/water to provide the title compound (1.21 g, 53%). $^1$H NMR (400 MHz, CDCl$_3$) δ 8.93 (br s, 1H), 7.55–7.33 (m, 11H), 7.15–7.11 (m, 2H), 5.03 (s, 2H), 4.29 (q, J=7.1 Hz, 2H), 1.24 (t, J=7.1 Hz, 3H).

c) ethyl 5-benzyloxy-1-(2-chloro-4,5-methylenedioxybenzyl)-3-phenylindole-2-carboxylate To a stirring suspension of sodium hydride (36.3 mg (60% in mineral oil), 0.91 mmol) in DMF (1.5 mL) was added the compound of Example 1(b) (270 mg, 0.73 mmol). After 10 min, 6-chloropiperonyl chloride (186 mg, 0.91 mmol) was added. After 1 h, the mixture was partitioned between water and ethyl acetate. The organic layer was washed with water and saturated brine, dried (MgSO$_4$), filtered and concentrated to leave an oily pale yellow solid. The solid was recrystallized from ethanol to provide the title compound (250 mg, 64%). $^1$H NMR (400 MHz, CDCl$_3$) δ 7.48–7.30 (m, 10H), 7.20 (br d, J=9.7 Hz, 1H), 7.12–7.08 (m, 2H), 6.90 (s, 1H), 6.01 (s, 1H), 5.89 (s, 2H), 5.76 (s, 2H), 5.02 (s, 2H), 4.13 (q, J=7.1 Hz, 2H), 1.00 (t, J=7.1 Hz, 3H).

d) 5-benzyloxy-1-(2-chloro-4,5-methylenedioxybenzyl)-3-phenylindole-2-carboxylic acid The compound of Example 1(c) (125 mg, 0.23 mmol) was dissolved in 1.5 mL of 1:1 THF/ethanol and 3 N potassium hydroxide (0.8 mL) was added. The mixture was heated at reflux for 1.5 h then diluted with ethyl acetate and acidified with 3 N HCl. The organic layer was washed with saturated brine, dried (MgSO$_4$), filtered and concentrated to provide the title compound (112 mg, 94%). mp 213°–214° C.

Example 2

Preparation of 5-benzyloxy-1-(4-benzyloxybenzyl)-3-phenylindole-2-carboxylic acid Following the procedure of Example 1(a)–1(d), except substituting 4-benzyloxybenzyl chloride for 6-chloropiperonyl chloride in step (c), the title compound was prepared (24% overall). mp(ethyl acetate/hexanes) 181°–182° C.

Example 3

Preparation of 1-(2-chloro-4,5-methylenedioxybenzyl)-3-phenylindole-2-carboxylic acid Following the procedure of Example 1(a)–1(d), except substituting ethyl indole-2-carboxylate for ethyl 5-benzyloxyindole-2-carboxylate in step (a), the title compound was prepared (42% overall). mp(ethyl acetate/hexanes) 226°–227° C.

Example 4

Preparation of 1-(4-benzyloxybenzyl)-3-phenylindole-2-carboxylic acid

Following the procedure of Example 1(a)–1(d), except substituting ethyl indole-2-carboxylate for ethyl 5-benzyloxyindole-2-carboxylate in step (a) and 4-benzyloxybenzyl chloride for 6-chloropiperonyl chloride in step (c), the title compound was prepared (39% overall). mp 193°–194° C.

Example 5

Preparation of 1-(2-chloro-4,5-methylenedioxybenzyl)-3-(4-methoxyphenyl)indole-2-carboxylic acid Following the procedure of Example 1(a)–1(d), except substituting ethyl indole-2-carboxylate for ethyl 5-benzyloxyindole-2-carboxylate in step (a) and 4-methoxyphenylboronic acid for phenylboronic acid in step (b), the title compound was prepared (92% overall). mp 189°–190° C.

Example 6

Preparation of 1-(2-chloro-4,5-methylenedioxybenzyl)-3-(1-naphthyl)indole-2-carboxylic acid a) ethyl 3-bromoindole-2-carboxylate Following the procedure of Example 1(a), except substituting ethyl indole-2-carboxylate for ethyl 5-benzyloxyindole-2-carboxylate, the title compound was prepared (94%). $^1$H NMR (400 MHz, CDCl$_3$) δ 9.07 (br s, 1H), 7.69 (d, J=7.7 Hz, 1H), 7.43–7.37 (m, 2H), 7.26–7.23 (m, 1H), 4.48 (q, J=7.2 Hz, 2H), 1.47 (t, J=7.2 Hz, 3H).

b) ethyl 3-bromo-1-(2-chloro-4,5-methylenedioxybenzyl)indole-2-carboxylate

Following the procedure of Example 1(c), except substituting ethyl 3-bromoindole-2-carboxylate for ethyl 5-benzyloxy-3-phenylindole-2-carboxylate, the title compound was prepared (71%). $^1$H NMR (400 MHz, CDCl$_3$) δ 7.74 (d, J=8.1 Hz, 1H), 7.39–7.36 (m, 1H), 7.29–7.24 (m, 2H), 6.89 (s, 1H), 5.88 (s, 2H), 5.87 (s, 1H), 5.75 (s, 2H), 4.40 (q, J=7.1 Hz, 2H), 1.39 (t, J=7.1 Hz, 3H).

c) Ethyl 1-(2-chloro-4,5-methylenedioxyphenylmethyl)-3-(1-naphthyl)indole-2-carboxylate Following the procedure of Example 1(b), except substituting ethyl 3-bromo-1-(2-chloro-4,5-methylenedioxybenzyl)indole-2-carboxylate for ethyl 5-benzyloxy-3-bromoindole-2-carboxylate and 1-naphthylboronic acid for phenylboronic acid, the title compound was prepared (77%). $^1$H NMR (250 MHz, CDCl$_3$) δ 7.92 (d, J=10.0 Hz, 2H), 7.67–7.45 (m, 4H), 7.40–7.32 (m, 4H), 7.16–7.09 (m, 1H), 6.12 (s, 1H), 5.96 (d, J=17.5 Hz, 1H), 5.92 (s, 2H), 5.87 (d, J=17.5 Hz, 1H), 3.82 (q, J=7.1 Hz, 2H), 0.43 (t, J=7.1 Hz, 3H).

d) 1-(2-chloro-4,5-methylenedioxyphenylmethyl)-3-(1-naphthyl)indole-2-carboxylic acid Following the procedure of Example 1(d), except substituting ethyl 1-(2-chloro-4,5-methylenedioxybenzyl)-3-(1-naphthyl)indole-2-carboxylate for ethyl 5-benzyloxy-1-(2-chloro-4,5-methylenedioxybnezyl)-3-phenylindole-2-carboxylate, the title compound was prepared (94%). mp 241°–242° C.

Example 7

Preparation of 1-(2-chloro-4,5-methylenedioxyphenylmethyl)-3-(3,5-dichlorophenyl)indole-2-carboxylic acid Following the procedure of Example 6(a)–6(d), except substituting 3,5-dichlorophenylboronic acid for 1-naphthylboronic acid in step (c), the title compound was prepared (51% overall). mp 221°–222° C.

Example 8

Preparation of 3-(3-chloro-4-fluorophenyl)-1-(2-chloro-4,5-methylenedioxyphenylmethyl)indole-2-carboxylic acid Following the procedure of Example 6(a)–6(d), except substituting 3-chloro-4-fluorophenylboronic acid for 1-naphthylboronic acid in step (c), the title compound was prepared (25% overall). mp 210°–211° C.

Example 9

Preparation of 1-(2-chloro-4,5-methylenedioxybenzyl)-3-phenyl-5-propyloxyindole-2-carboxylic acid a) ethyl 1-(2-chloro-4,5-methylenedioxybenzyl)-5-hydroxy-3-phenylindole-2-carboxylate The compound of example 6(c) (3.6 g, 6.67 mmol) was dissolved in ethyl acetate (200 mL) and to the solution was added 10% palladium on carbon (1.8 g, 50% w/w). The mixture was placed on a Parr shaker at 60 p.s.i. for 16 hours, then filtered through Celite. The solution was concentrated to give a residue that was purified by column chromatography (silica gel, ethyl acetate/hexane) to give the title compound as a white solid (2.47 g, 82%). $^1$HNMR (400 MHz, CDCl$_3$) δ 7.46 (m, 4H), 7.15 (m, 2H), 6.92 (m, 3H), 6.00 (s, 1H), 5.89 (s, 2H), 5.73 (s, 2H), 4.69 (s, 1H), 4.11 (q, 2H), 0.99 (t, 3H).

b) ethyl 1-(2-chloro-4,5-methylenedioxybenzyl)-3-phenyl-5-propyloxyindole-2-carboxylate To a stirring suspension of sodium hydride (0.010 g, (60% in mineral oil), 0.250 mmol) in DMF (1.5 mL) was added the compound of Example 9(a) (0.075 g, 0. 167 mmol). After 15 minutes, 3-bromopropane (0.023 g, 0.184 mmol) was added. After 1.5 hours, the mixture was partitioned between water and ethyl acetate. The organic layer was washed with water and saturated brine, dried (MgSO$_4$), filtered and concentrated to a residue that was purified by column chromatography (ethyl acetate/hexane) to give the title compound as a white solid (0.064 g, 78%). $^1$HNMR (400 MHz, CDCl$_3$) δ 7.45 (m, 5H), 7.19 (m, 1H), 7.04 (m, 2H), 6.90 (s, 1H), 6.00 (s, 1H), 5.88 (s, 2H), 5.75 (s, 2H), 4.12 (q, 2H), 3.88 (t, 2H), 1.80 (m, 2H), 1.03 (m, 6H).

c) 1-(2-chloro-4,5-methylenedioxybenzyl)-3-phenyl-5-propyloxyindole-2-carboxylic acid Following the procedure of Example 1(d) except substituting ethyl 1-(2-chloro-4,5-methylenedioxybenzyl)-3-phenyl-5-propyloxyindole-2-carboxylate for ethyl 5-benzyloxy-1-(2-chloro-4,5-methylenedioxybenzyl)-3-phenylindole-2-carboxylate, the title compound was prepared as a white solid (0.053 g, 88%). The title compound was converted to the sodium salt using 1.0 eq of 0.1N sodium hydroxide in ethanol. MS (MH$^+$): 464.0.

Example 10

Preparation of 1-(2-chloro-4,5-methylenedioxyphenylmethyl)-3-arylindole-2-carboxylic acid ten member sublibrary a) 3-Bromoindole-2-carboxylic acid A solution of ethyl 3-bromoindole-2-carboxylate (54.40 g, 203 mmol) in EtOH (600 ml) and water (50 ml) with NaOH (20.20 g, 505 mmol) was refluxed for 1 h. The mixture was cooled and the sodium salt of the title compound was removed by filtration. This was acidified (aqueous 3N HCl) and extracted with ethyl acetate. The organic extract was washed with water then brine, dried (sodium sulfate) and concentrated. Crystallization from ethyl acetate afforded the product (47.1 g, 88%). mp 201°–203° C.

b) Wang resin supported 3-bromoindole-2-carboxylate

To a solution of 3-bromoindole-2-carboxylic acid (50.0 g, 208 mmol) in DMF (700 ml) with 1-hydroxybenzotriazole (28.1 g, 208 mmol) was added 1,3-diisopropylcarbodiimide (26.23 g, 208 mmol). After stirring 30 min at room temperature, the mixture was filtered and to the filtrate was added Wang resin (0.72 meq/g) (72 g, 51.8 mmol). After stirring 10 min 4-dimethylaminopyridine (25.4 g, 208 mmol) was added and stirring continued for 7 days at room temperature. The mixture was filtered and resin was washed successively with DMF (3×1 l), methanol (3×1 l) water (3×1 l) and methanol (3×1 l) then dried at 50° C. in vacuo.

c) Wang resin supported 3-phenylindole-2-carboxylate

The resin-bound compound of example 10(b) (2.0 g, 96 mmol), phenylboronic acid (0.70 g, 5.7 mmol) and tetrakis (triphenylphosphine)palladium(0) (150 mg, 0.13 mmol) were combined and to the mixture was added toluene (25 ml), ethanol (5 ml) and 2 N sodium carbonate (5 ml). The mixture was heated with stirring at 90° C. for 17 h, then cooled to room temperature and filtered. The resin was washed successively with DMF (3×75 ml), methanol (3×75 ml) water (3×75 ml) and methanol (3×75 ml) then dried at 50° C. in vacuo.

d) Ten component Wang resin supported 3-arylindole-2-carboxylate mixture

The procedure of example 10(c) was repeated nine times with phenylboronic acid replaced by one of the following arylboronic acids; 4-chlorophenylboronic acid, 4-trifluoromethylphenylboronic acid, 4-biphenylboronic acid, 4-phenoxyphenylboronic acid, 4-methoxyphenylboronic acid, 3-chloro-4-fluorophenylboronic acid, 1-naphthylboronic acid, 3,5-dichlorophenylboronic acid, 2,4-dimethoxyphenylboronic acid. The resins were combined and added to methanol and the resulting slurry stirred for 20 min. The solvent was removed and the resin dried in vacuo.

e) Ten component Wang resin supported 1-(2-chloro-4,5-methylenedioxyphenylmethyl)-3-arylindole-2-carboxylate mixture The mixture of Example 10(d) (1.25 g, ca. 0.6 mil) was slurried in dry DMF (30 ml) at room temperature. To this was added a slurry of NaH (140 mg of 60% oil dispersion, 3.5 mmol) in DMF (10 ml) and stirring continued for 18 h. To this was added a solution of 6-chloropiperonyl chloride (718 mg, 3.5 mmol) in DMF (5 ml) and stirring continued 20 h. The mixture was filtered and the resin was washed successively with DMF (3×50 ml), methanol (3×50 ml) water (3×50 ml) and methanol (3×50 ml) then dried at 50° C. in vacuo.

f) 1-(2-chloro-4,5-methylenedioxyphenylmethyl)-3-arylindole-2-carboxylic acid ten member sublibrary The mixture of Example 10(e) (414 mg, ca. 0.2 mmol) was stirred in DMF (10 ml) with 5M aqueous sodium hydroxide solution (1 ml) at room temperature for 20 h. The mixture was filtered and the filtrate partitioned between 3N HCl and ethyl acetate. The organic extract was washed with water then brine, dried (sodium sulfate) and the solvent removed in vacuo to afford the title sublibrary (37 mg). MS m/e (M-H)$^-$: 404.0, 434.0, 438.0, 454.0, 455.8, 463.8, 471.8, 479.8, 495.8.

Example 11

Preparation of 3-aryl-1-(3,5-dimethoxyphenylmethyl) indole-2-carboxylic acid ten member sublibrary Following the procedure of Examples 10(a)–10(f), with the exception of substitution of 3,5-dimethoxybenzyl chloride for 6-chloropiperonyl chloride in step (e), the title sub library was prepared (30 mg). MS m/e (M-H)$^-$: 386.0, 416.0, 420.0, 436.0, 438.0, 446.0, 454.0, 462.0, 478.0.

Example 12

Preparation of 3-aryl-1-(2-methoxy-5-nitrophenylmethyl) indole-2-carboxylic acid ten member sublibrary Following the procedure of Examples 10(a)–10(f), with the exception of substitution of 2-methoxy-5-nitrobenzyl bromide for 6-chloropiperonyl chloride in step (e), the title sublibrary was prepared (40 mg). MS m/e (M-H)$^-$: 401.0, 431.0, 435.0, 451.0, 453.0, 461.0, 469.0, 477.0, 493.0.

Example 13

Preparation of 3-aryl-1-phenylmethylindole-2-carboxylic acid ten member sublibrary Following the procedure of Examples 10(a)–10(f), with the exception of substitution of benzyl chloride for 6-chloropiperonyl chloride in step (e), the title sublibrary was prepared (31 mg). MS m/e (M-H)$^-$: 326.0, 356.0, 360.0, 376.0, 377.8, 386.0, 394.0, 402.0, 418.0.

Example 14

Preparation of 3-aryl-1-(4-methylphenylmethyl)indole-2-carboxylic acid ten member sublibrary Following the procedure of Examples 10(a)–10(f), with the exception of substitution of 4-methylbenzyl bromide for 6-chloropiperonyl chloride in step (e), the title sublibrary was prepared (48 mg). MS m/e (M-H)$^-$: 340.0, 370.0, 374.0, 390.0, 391.8, 400.0, 408.0, 416.0, 432.2.

Example 15

Preparation of 3-aryl-1-(4-benzyloxyphenylmethyl)indole-2-carboxylic acid ten member sublibrary Following the procedure of Examples 10(a)–10(f), with the exception of substitution of 4-benzyloxybenzyl chloride for 6-chloropiperonyl chloride in step (e), the title sublibrary was prepared (35 mg). MS m/e (M-H)$^-$: 432.0, 462.2, 466.2, 482.0, 484.0, 492.2, 500.0, 508.4, 524.0.

Example 16

Preparation of 3-aryl-1-(4-methoxyphenylmethyl)indole-2-carboxylic acid ten member sublibrary Following the procedure of Examples 10(a)–10(f), with the exception of substitution of 4-methoxybenzyl chloride for 6-chloropiperonyl chloride in step (e), the title sublibrary was prepared (35 mg). MS m/e (M-H)$^-$: 356.0, 386.0, 390.0, 406.0, 408.0, 416.0, 424.0, 432.0, 448.2.

Example 17

Preparation of 3-aryl-1-(4-trifluoromethoxyphenylmethyl) indole-2-carboxylic acid ten member sublibrary Following the procedure of Examples 10(a)–10(f), with the exception of substitution of 4-trifluoromethoxybenzyl bromide for 6-chloropiperonyl chloride in step (e), the title sublibrary was prepared (31 mg). MS m/e (M-H)$^-$: 410.0, 440.0, 444.0, 460.0, 470.0, 478.0, 486.0, 502.0.

Example 18

Preparation of 1-(2-chloro-4,5-methylenedioxybenzyl)-5-(2-isopropyloxy)-3-phenylindole-2-carboxylic acid a) ethyl 1-(2-chloro-4,5-methylenedioxybenzyl)-5-(2-isopropyloxy)-3-phenylindole-2-carboxylate The compound of Example 9(a) (0.100 g, 0.222 mmol), isopropanol (0.016 g, 0.267 mmol), and triphenylphosphine (0.070 g, 0.267 mmol) were dissolved in THF (2 mL) and taken to 0° C. when diisopropylazodicarboxylate (0.054 g, 0.267 mmol) was added dropwise. The solution was allowed to warm to room temperature and stir for 16 hours when concentrated. The resulting residue was chromatographed (silica gel, ethyl acetate/hexane) to provide the title compound as a white solid (0.078 g, 71%). $^1$HNMR (400 MHz, CDCl$_3$) δ 7.65 (d, 2H), 7.55 (d, 2H), 7.47 (m, 5H), 7.21 (m, 1H), 7.11–7.05 (m, 2H), 6.90 (s, 1H), 6.02 (s, 1H), 5.89 (s, 2H), 5.77 (s, 2H), 5.05 (s, 2H), 4.18 (q, 2H), 1.08 (t, 3H).

b) 1-(2-chloro-4,5-methylenedioxybenzyl)-5-(isopropyloxy)-3-phenylindole-2-carboxylic acid Following the procedure of Example 1(d) except substituting ethyl 1-(2-chloro-4,5-methylenedioxybenzyl)-5-(2-isopropyloxy)-3-phenylindole-2-carboxylate for ethyl 5-benzyloxy-1-(2-chloro-4,5-methylenedioxybenzyl)-3-phenylindole-2-carboxylate, the title compound was prepared as a white solid (0.070 g, 95%). MS (MH$^-$): 462.0

Example 19

Preparation of 1-(2-chloro-4,5-methylenedioxybenzyl)-3-phenyl5-(4-trifluoromethylbenzyloxy)indole-2-carboxylic acid Following the procedure of Example 18(a)–18(b), except substituting 4-trifluoromethylbenzyl alcohol for isopropanol in step (a), the title compound was prepared (0.064 g, 52% overall). MS (MH$^-$): 578.0

Example 20

Preparation of 1-(2-chloro-4,5-methylenedioxybenzyl)-3-phenyl-5-(3-trifluoromethylbenzyloxy)indole-2-carboxylic acid Following the procedure of Example 18(a)–18(b), except substituting 3-trifluoromethylbenzyl alcohol for isopropanol in step (a), the title compound was prepared (0.058 g, 33% overall). MS (MH$^-$): 578.0

Example 21

Preparation of 1-(2-chloro-4,5-methylenedioxybenzyl)-5-(3,4-methylenedioxybenzyloxy)-3-phenylindole-2-carboxylic acid Following the procedure of Example 18(a)–18(b), except substituting piperonyl alcohol for isopropanol in step (a), the title compound was prepared (0.042 g, 52% overall). MS (MH⁻): 554.0

Example 22

Preparation of 1-(2-chloro-4,5-methylenedioxybenzyl)-5-(4-methoxybenzyloxy)-3-phenylindole-2-carboxylic acid Following the procedure of Example 18(a)–18(b), except substituting 4-methoxybenzyl alcohol for isopropanol in step (a), the title compound was prepared (0.060 g, 50% overall). MS (MH⁻): 540.0

Example 23

Preparation of 1-(2-chloro-4,5-methylenedioxybenzyl)-5-cyclohexylmethoxy-3-phenylindole-2-carboxylic acid Following the procedure of Example 18(a)–18(b), except substituting cyclohexylmethanol for isopropanol in step (a), the title compound was prepared (0.020 g, 17% overall). MS (MH⁺): 518.0

Example 24

Preparation of 1-(2-chloro-4,5-methylenedioxybenzyl)-3-phenyl-5-(2-trifluoromethylbenzyloxy)indole-2-carboxylic acid Following the procedure of Example 18(a)–18(b), except substituting 2-trifluoromethylbenzyl alcohol for isopropaonl in step (a), the title compound was prepared (0.031 g, 24% overall). MS (MH⁻): 578.0

Example 25

Preparation of 1-(2-chloro-4,5-methylenedioxybenzyl)-3-(4-methylphenyl)-5-(4-methylthiobenzyloxy)indole-2-carboxylic acid a) ethyl 1-(2-chloro-4,5-methylenedioxybenzyl)-5-hydroxy-3-(4-methylphenyl)indole-2-carboxylate Following the procedure of Example 1(a)–1(c) except substituting 4-methylphenylboronic acid for phenylboronic acid in step (b), and the procedure of Example 9(a), except substituting ethyl 5-benzyloxy-1-(2-chloro-4,5-methylenedioxybenzyl)-3-(4-methylphenyl)indole-2-carboxylate for ethyl 5-benzyloxy-1-(2-chloro-4,5-methylenedioxybenzyl)-3-phenylindole-2-carboxylate, the title compound was prepared as a white solid (0.304 g, 81%). ¹HNMR (400 MHz, CDCl₃) δ 7.37 (m, 2H), 7.24 (s, 1H), 7.15 (d, 1H), 6.97 (m, 3H), 6.00 (s, 1H), 5.89 (s, 2H), 5.71 (s, 2H), 4.56 (s, 1H), 4.13 (q, 2H), 2.43 (s, 3H), 1.03 (t, 3H).

b) 1-(2-chloro-4,5-methylenedioxybenzyl)-3-(4-methylphenyl)-5-(4-methylthiobenzyloxy)indole-2-carboxylic acid Following the procedure of Example 18(a)–18(b), except substituting ethyl 1-(2-chloro-4,5-methylenedioxybenzyl)-5-hydroxy-3-(4-methylphenyl)indole-2-carboxylate for ethyl 1-(2-chloro-4,5-methylenedioxybenzyl)-5-hydroxy-3-phenylindole-2-carboxylate and 4-methylthiobenzyl alcohol for isopropanol in step (a), the title compound was prepared as a white solid (38% overall). MS (MH⁻): 570.0

Example 26

Preparation of 1-(2-chloro-4,5-methylenedioxybenzyl)-3-(3,5-dichlorophenyl)-5-(4-trifluoromethoxybenzyloxy)indole-2-carboxylic acid a) ethyl 5-benzyloxy-1-(2-chloro-4,5-methylenedioxybenzyl)-3-(3,5-dichlorophenyl)indole-2-carboxylate Following the procedure of Example 1(a)–1(c), except substituting 3,5-dichlorophenylboronic acid for phenylboronic acid in step (b) the title compound was prepared as a white solid (7.37 g, 73%) ¹HNMR (400 MHz, CDCl₃) δ 7.40(m, 8H), 7.23 (m, 1H), 7.12 (m, 1H), 7.01 (m, 1H), 6.91 (s, 1H), 5.95 (s, 1H), 5.90 (s, 2H), 5.77 (s, 2H), 5.05 (s, 2H), 4.18 (q, 2H), 1.08 (t, 3H).

b) ethyl 1-(2-chloro-4,5-methylenedioxybenzyl)-3-(3,5-dichlorophenyl)-5-hydroxyindole-2-carboxylate Following the procedure of Example 9(a), except substituting ethyl 5-benzyloxy-1-(2-chloro-4,5-methylenedioxybenzyl)-3-(3,5-dichlorophenyl)indole-2-carboxylate for ethyl 5-benzyloxy-1-(2-chloro-4,5-methylenedioxybenzyl)-3-phenylindole-2-carboxylate, the title compound was prepared as a white solid (3.47 g, 64%). ¹HNMR (400 MHz, CDCl₃) δ 7.36 (m, 3H), 7.17 (d, 1H), 6.96 (m, 2H), 6.90 (s, 1H), 5.95 (s, 1H), 5.90 (s, 2H), 5.74 (s, 2H), 4.71 (s, 1H), 4.18 (q, 2H), 1.08 (t, 3H).

c) ethyl 1-(2-chloro-4,5-methylenedioxybenzyl)-3-(3,5-dichlorophenyl)-5-(4-trifluoromethoxybenzyloxy)indole-2-carboxylate To the compound of Example 26(b) (0.110 g, 0.212 mmol) in THF (2 mL) was added potassium bis (trimethylsilyl)amide (0.636 mL (0.5M in toluene), 0.316 mmol). The solution stirred at room temperature for 1 hour when 4-trifluoromethoxybenzyl bromide (0.065 g, 0.254 mmol) was added and stirring continued for 4 hours. The solution was partitioned between ethyl acetate and water. The aqueous layer was extracted with ethyl acetate and then the organic layers were combined, dried over MgSO₄, filtered and concentrated to a residue that was purified by column chromatography (silica gel, ethyl acetate/hexane) to give the title compound as a white solid (0.073 g, 50%). ¹HNMR (400 MHz, CDCl₃) δ 7.48 (m, 2H), 7.41 (m, 1H), 7.37 (m, 2H), 7.27–7.21 (m, 3H), 7.11 (m, 1H), 7.09 (m, 1H), 6.90 (s, 1H), 5.94 (s, 1H), 5.90 (s, 2H), 5.77 (s, 2H), 5.05 (s, 2H), 4.17 (q, 2H), 1.09 (t, 3H).

d) 1-(2-chloro-4,5-methylenedioxybenzyl)-3-(3,5-dichlorophenyl)-5-(4-trifluoromethoxybenzyloxy)indole-2-carboxylic acid Following the procedure of Example 1(d), except substituting ethyl 1-(2-chloro-4,5-methylenedioxybenzyl)-3-(3,5-dichlorophenyl)-5-(4-trifluoromethoxybenzyloxy)indole-2-carboxylate for ethyl 5-benzyloxy-1-(2-chloro-4,5-methylenedioxybenzyl)-3-phenylindole-2-carboxylate, the title compound was prepared as a white solid (42% overall). MS (MH⁻): 662.0

Example 27

Preparation of 1-(2-chloro-4,5-methylenedioxybenzyl)-5-(2-chloro-4,5-methylenedioxybenzyloxy)-3-(3,5-dichlorophenyl)indole-2-carboxylic acid Following the procedure of Example 26(a)–26(d), except substituting 6-chloropiperonyl chloride for 4-trifluoromethoxybenzyl bromide in step (c), the title compound was prepared as a white solid (49% overall). MS (MH⁻): 656.0

Example 28

Preparation of 5-(4-tert-butyl)benzyloxy)-1-(2-chloro-4,5-methylenedioxybenzyl)-3-phenylindole-2-carboxylic acid Following the procedure of Example 26(c)–26(d), except substituting ethyl 1-(2-chloro-4,5-methylenedioxybenzyl)-5-hydroxy-3-phenylindole-2-carboxylate for ethyl 1-(2-chloro-4,5-methylenedioxybenzyl)-3-(3,5-dichlorophenyl)-

Example 29

Preparation of 1-(2-chloro-4,5-methylenedioxybenzyl)-5-(3-methoxybenzyloxy)-3-phenylindole-2-carboxylic acid Following the procedure of Example 26(c)–26(d), except substituting ethyl 1-(2-chloro-4,5-methylenedioxybenzyl)-5-hydroxy-3-phenylindole-2-carboxylate for 1-(2-chloro-4,5-methylenedioxybenzyl)-3-(3,5-dichlorophenyl)-5-hydroxyindole-2-carboxylate and 3-methoxybenzyl chloride for 4-trifluoromethoxybenzyl bromide in step (c), the title compound was prepared as a white solid (64% overall). MS (MH+): 542.4

Example 30

Preparation of 1-(2-chloro-4,5-methylenedioxybenzyl)-5-[4-(2,2-dimethylpropanoyl)benzyloxyl]-3-phenylindole-2-carboxylic acid Following the procedure of Example 9(b)–9(c), except substituting (2,2-dimethylpropanoyl)benzyl bromide for 3-bromopropane in step (b), the title compound was prepared (58% overall). MS (MH−): 594.0

Example 31

Preparation of 1-(2-chloro-4,5-methylenedioxybenzyl)-5-(2-methoxybenzyloxy)-3-phenylindole-2-carboxylic acid Following the procedure of Example 18(a)–18(b), except substituting 2-methoxybenzyl alcohol for isopropanol in step (a), the title compound was prepared (30% overall). MS (MH−): 540.0

Example 32

Preparation of 1-(2-chloro-4,5-methylenedioxyphenylmethyl)-5-(4-cyanophenylmethoxy)-3-phenylindole-2-carboxylic acid Following the procedure of Example 26(c)–26(d), except substituting ethyl 1-(2-chloro-4,5-methylenedioxyphenylmethyl)-5-hydroxy-3-phenylindole-2-carboxylate for 1-(2-chloro-4,5-methylenedioxybenzyl)-3-(3,5-dichlorophenyl)-5-hydroxyindole-2-carboxylate and 4-cyanobenzyl bromide for 4-trifluoromethoxybenzyl bromide in step (c), the title compound was prepared as a white solid (41% overall). MS (MH−): 535.0

Example 33

Preparation of 1-(2-chloro-4,5-methylenedioxybenzyl)-5-(2-chloro-4,5-methylenedioxybenzyloxy)-3-phenylindole-2-carboxylic acid Following the procedure of Example 9(b)–9(c), except substituting 6-chloropiperonyl chloride for 3-bromopropane in step (b), the title compound was prepared (65% overall). MS (MH+): 587.0

Example 34

Preparation of 1-(2-chloro-4,5-methylenedioxyphenylethyl)-5-(4-methylthiophenylmethoxy-3-phenylindole-2-carboxylic acid Following the procedure of Example 9(b)–9(c), except substituting 4-methylthiobenzyl bromide for 3-bromopropane in step (b), the title compound was prepared (70% overall). MS (MH+): 558.0

Example 35

Preparation of 1-(2-chloro-4,5-methylenedioxyphenylethyl)-3-(4-formylphenyll)-5-phenylmethoxyindole-2-carboxylic acid Following the procedure of Example 1(a)–1(d), except substituting 4-formylphenylboronic acid for phenylboronic acid in step (b), the title compound was prepared as a white solid (76% overall). MS (MH−): 538.0

Example 36

Preparation of 5-benzloxy-1-(2-chloro-4,5-methylenedioxybenzyl)-3-(2-formylphenyl)indole-2-carboxylic acid Following the procedure of Example 1(a)–1(d), except substituting 2-formylphenylboronic acid for phenylboronic acid in step (b), the title compound was prepared as a white solid (54% overall). MS (MH−): 538.2

Example 37

Preparation of 5-benzloxy-1-(2-chloro-4,5-methylenedioxybenzyl)-3-(4-fluorophenyl)indole-2-carboxylic acid Following the procedure of Example 1(a)–1(d), except substituting 4-fluorophenylboronic acid for phenylboronic acid in step (b), the title compound was prepared as a white solid (77% overall). MS (MH−): 428.0

Example 38

Preparation of 3-(3-aminophenyl)-5-benzloxy-1-(2-chloro-4,5-methylenedioxybenzyl)indole-2-carboxylic acid Following the procedure of Example 1(a)–1(d), except substituting 3-aminophenylboronic acid for phenylboronic acid in step (b), the title compound was prepared as a yellow solid (65% overall). MS (MH−): 525.0

Example 39

Preparation of 5-benzloxy-1-(2-chloro-4,5-methylenedioxybenzyl)-3-(2,4-dichlorophenyl)indole-2-carboxylic acid Following the procedure of Example 1(a)–1(d), except substituting 2,4-dichlorophenylboronic acid for phenylboronic acid in step (b), the title compound was prepared as a white solid (63% overall). MS (MH−): 578.2

Methods of Treatment

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokine is IL-8.

The compounds of Formula (I) are administered in an amount sufficient to inhibit cytokine function, in particular IL-8, such that it's biologically regulated down to normal levels of physiological function, or in some case to subnormal levels, so as to ameliorate the disease state. Abnormal levels of IL-8, for instance in the context of the present invention, constitute: (i) levels of free IL-8 greater than or equal to 1 picogram per ml; (ii) any cell associated IL-8 above normal physiological levels; or (iii) the presence of IL-8 above basal levels in cells or tissues in which IL-8, respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, allograft rejections, and malaria.

These diseases are primarily characterized by massive neutrophil infiltration, and are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 induced chemotaxis or activation would lead to a direct reduction in the neutrophil infiltration.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be dual inhibitors of both recombinant type I and type II IL-8 receptors.

As used herein, the term "IL-8 mediated disease or disease state" refers to any and all disease states in which IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 $\alpha$ or $\beta$ receptor plays a role, such as but not limited to IL-8, GRO-$\alpha$, GRO-$\beta$, GRO-$\gamma$, or NAP-2. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-$\alpha$) and Tumor Necrosis Factor beta (TNF-$\beta$).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to, IL-8, GRO-$\alpha$, GRO-$\beta$, GRO-$\gamma$, NAP-2, IP-10, MIP-1$\alpha$, MIP-$\beta$, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8 cytokine-inhibiting effects of compounds of the present invention were determined by the following in vitro assay:

Receptor Binding, Assays

[$^{125}$I] IL-8 (human recombinant) was obtained from Amersham Corp., Arlington Heights, Ill., with specific activity 2000 Ci/mmol. All other chemicals were of analytical grade. High levels of recombinant human IL-8 type $\alpha$ and $\beta$ receptors were individually expressed in Chinese hamster ovary cells as described previously (Holmes, et al., *Science*, 1991, 253, 1278). The Chinese hamster ovary membranes were homogenized according to a previously described protocol (Kraft, et al., *Nature*, 1983, 301, 621). Membrane protein concentration was determined using Pierce Co. micro-assay kit using bovine serum albumin as a standard. All assays were performed in a 96-well micro plate format. Each reaction mixture contained $^{125}$I IL-8 (0.25 nM), 0.5 µg/mL of IL-8R$\alpha$ or 1.0 µg/mL of IL-8R$\beta$ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS plus peptide at relevant concentrations. The assay was initiated by addition of $^{125}$I-IL-8. After 1 hour at room temperature the plate was harvested using a Tomtec 96-well harvester onto a glass fiber filtermat blocked with 1% polyethyleneimine/0.5% BSA and washed 3 times with 25 mM NaCl, 10 mM TrisHCl, 1 mM MgSO$_4$, 0.5 mM EDTA, 0.03% CHAPS, pH 7.4. The filter was then dried and counted on the Betaplate liquid scintillation counter. The recombinant IL-8Rα, or Type I, receptor is also referred to herein as the non-permissive receptor and the recombinant IL-8Rβ, or Type II, receptor is referred to as the permissive receptor.

The compounds of Formula (II) tested as sublibraries (IIa) thru (IIh), and representative compounds of Formula (I) as noted herein by Examples 1 to 9, all demonstrated an $IC_{50}$ from about 11 to about 71 µM in the non-permissive and permissive models for IL-8 receptor inhibition. However, the compound of formula (Ib) as illustrated herein, when R is H and Ar is unsubstituted phenyl has been found not active in the above assay.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chemokine mediated disease state, wherein the chemokine binds to an IL-8 α or β receptor in a mammal, which comprises administering to said mammal an effective amount of a compound of the formula

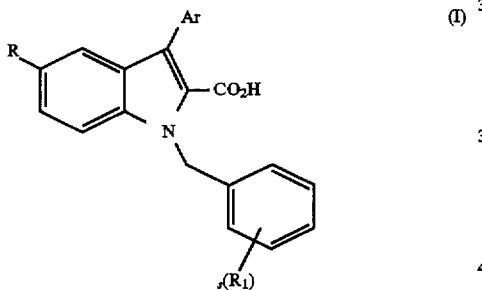

wherein

Ar is an optionally substituted phenyl or naphthyl group;

R is hydrogen, hydroxy, $C_{1-8}$ alkoxy, or O—$(CR_8R_9)_n$—$R_6$;

$R_6$ is an optionally substituted $C_{3-7}$ cycloalkyl, optionally substituted $C_{3-7}$ cycloalkenyl, or optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$ alkoxy, halosubstituted$C_{1-8}$ alkoxy, O—$CH_2$—O—$C_{1-8}$alkyl, —$(CH_2)_t$aryl, O—$(CH_2)_t$ aryl, —O—$(CH_2)_v$C(O)O$C_{1-4}$alkyl, $NO_2$, $S(O)_mR_2$, $N(R_3)_2$, NHC(O)$R_4$, —C(O)$R_5$, or together two $R_1$ moieties may form a methylene dioxy ring system, or together two $R_1$ moieties may form a 6 membered saturated or unsaturated ring system which may be optionally substituted;

t is 0 or an integer having a value of 1, 2, 3, or 4;

v is an integer having a value of 1, 2, 3, or 4;

s is an integer having a value of 1, 2, or 3;

m is 0 or an integer having a value of 1 or 2;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl;

$R_5$ is hydrogen, optionally substituted $C_{1-8}$ alkyl, or $C_{1-8}$ alkoxy;

$R_8$ and $R_9$ are independently hydrogen or $C_{1-4}$ alkyl;

or pharmaceutically acceptable salts thereof.

2. The method according to claim 1 wherein the chemokine is IL-8.

3. The method according to claim 2 wherein the mammal is afflicted with an IL-8 mediated disease selected from psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, or toxic shock syndrome glomerulonephritis, graft vs. host reaction, allograft rejections, and malaria.

4. A method of treating a chemokine mediated disease wherein the disease is inflammation in a mammal in need thereof, which comprises administering to said mammal an effective amount of a compound of Formula (I)

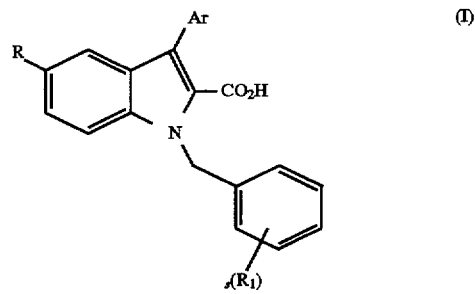

wherein

Ar is an optionally substituted phenyl or naphthyl group;

R is hydrogen, hydroxy, $C_{1-8}$ alkoxy, or O—$(CR_8R_9)_n$—$R_6$;

$R_6$ is an optionally substituted $C_{3-7}$ cycloalkyl, optionally substituted $C_{3-7}$ cycloalkenyl, or optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, O—$CH_2$—O—$C_{1-8}$alkyl, —$(CH_2)_t$aryl, O—$(CH_2)_t$ aryl, —O—$(CH_2)_v$C(O)O$C_{1-4}$alkyl, $NO_2$, $S(O)_mR_2$, $N(R_3)_2$, NHC(O)$R_4$, —C(O)$R_5$, or together two $R_1$ moieties may form a methylene dioxy ring system, or together two $R_1$ moieties may form a 6 membered saturated or unsaturated ring system which may be optionally substituted;

t is 0 or an integer having a value of 1, 2, 3, or 4;

v is an integer having a value of 1, 2, 3, or 4;

s is an integer having a value of 1, 2, or 3;

m is 0 or an integer having a value of 1 or 2;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl;

$R_5$ is hydrogen, optionally substituted $C_{1-8}$ alkyl, or $C_{1-8}$ alkoxy;

$R_8$ and $R_9$ are independently hydrogen or $C_{1-4}$ alkyl;

or a pharmaceutically acceptable salt thereof.

5. A method of treating a chemokine mediated disease wherein the disease is asthma in a mammal in need thereof, which comprises administering to said mammal an effective amount of a compound of Formula (I)

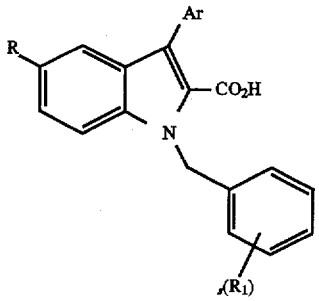

wherein

Ar is an optionally substituted phenyl or naphthyl group;

R is hydrogen, hydroxy, $C_{1-8}$ alkoxy, or $O-(CR_8R_9)_n-R_6$;

$R_6$ is an optionally substituted $C_{3-7}$ cycloalkyl, optionally substituted $C_{3-7}$ cycloalkenyl, or optionally substituted aryl;

n is 0 or an integer having a value of 1, 2, 3 or 4;

$R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, $O-CH_2-O-C_{1-8}$alkyl, $-(CH_2)_t$aryl, $O-(CH_2)_t$ aryl, $-O-(CH_2)_vC(O)OC_{1-4}$alkyl, $NO_2$, $S(O)_mR_2$, $N(R_3)_2$, $NHC(O)R_4$, $-C(O)R_5$, or together two $R_1$ moieties may form a methylene dioxy ring system, or together two $R_1$ moieties may form a 6 membered saturated or unsaturated ring system which may be optionally substituted;

t is 0 or an integer having a value of 1, 2, 3, or 4;

v is an integer having a value of 1, 2, 3, or 4;

s is an integer having a value of 1, 2, or 3;

m is 0 or an integer having a value of 1 or 2;

$R_2$ is an optionally substituted $C_{1-8}$ alkyl;

$R_3$ is independently hydrogen, or $C_{1-4}$ alkyl, or together with the nitrogen to which they are attached form a 5 to 7 membered saturated or unsaturated ring;

$R_4$ is independently hydrogen, or $C_{1-4}$ alkyl;

$R_5$ is hydrogen, optionally substituted $C_{1-8}$ alkyl, or $C_{1-8}$ alkoxy;

$R_8$ and $R_9$ are independently hydrogen or $C_{1-4}$ alkyl;

or a pharmaceutically acceptable salt thereof.

6. A compound according to claim 1 wherein the Ar is an optionally substituted phenyl.

7. A compound according to claim 6 wherein the substituents are independently chlorine, flourine, $CF_3$, phenyl, methyl, $-C(O)H$, amino, methoxy, phenoxy, or phenyl.

8. A compound according to claim 1 wherein R is an optionally substituted $O-(CR_8R_9)_n-R_6$.

9. A compound according to claim 8 wherein $R_6$ is an optionally substituted aryl ring.

10. A compound according to claim 9 wherein the aryl ring is substituted one or more times independently by halogen; hydroxy; hydroxy substituted $C_{1-10}$alkyl; $C_{1-10}$ alkyl; halosubstituted $C_{1-10}$ alkyl; $C_{1-10}$ alkoxy; optionally substituted $C_{1-10}$ alkoxy; $S-C_{1-10}$ alkyl; $N(R_3)_2$; $N(R_3)-C(O)C_{1-10}$alkyl; $C(O)C_{1-10}$alkyl; cyano, nitro; a methylene dioxy ring; an optionally substituted aryl; or an optionally substituted arylalkyl.

11. The compound according to claim 1 wherein $R_1$ is hydrogen, halogen, halosubstituted $C_{1-8}$ alkyl, $C_{1-8}$ alkyl, hydroxy, $C_{1-8}$alkoxy, halosubstituted$C_{1-8}$ alkoxy, $-(CH_2)_s$aryl, $O-(CH_2)_t$ aryl, $NO_2$; or together two $R_1$ moieties may form a methylene dioxy ring system.

12. The compound according to claim 11 wherein $R_1$ is hydrogen, 2-methoxy, 5-nitro, 4-methyl; 3,5-di-methoxy, 4-benzyloxy, 4-methoxy, 2-chloro-4,5-methylenedioxy, or 4-OCF$_3$.

13. A compound according to claim 1 wherein the compound, or its pharmaceutically acceptable salt is:

1-(2-chloro-4,5-methylenedioxyphenylmethyl)-3-(4-methoxyphenyl)indole-2-carboxylic acid;

1-(2-chloro-4,5-methylenedioxyphenylmethyl)-3-phenyl-5-phenylmethylindole-2-carboxylic acid;

1-(2-chloro-4,5-methylenedioxyphenylmethyl)-3-phenylindole-2-carboxylic acid;

1-(2-chloro-4,5-methylenedioxyphenylmethyl)-3-(1-naphthyl)indole-2-carboxylic acid;

1-(2-chloro-4,5-methylenedioxyphenylmethyl)-3-(3,5-dichlorophenyl)indole-2-carboxylic acid;

1-(2-chloro-4,5-methylenedioxyphenylmethyl)-3-(3-chloro-4-fluorophenyl)indole-2-carboxylic acid;

1-(2-Chloro-4,5-methylenedioxybenzyl)-3-phenyl-5-propyloxyindole-2-carboxylic acid 1-(2-Chloro-4,5-methylenedioxybenzyl)-3-phenyl-5-isopropyloxyindole-2-carboxylic acid 1-(2-Chloro-4,5-methylenedioxybenzyl)-3-phenyl-5-(4-trifluoromethylbenzyloxy)-indole-2-carboxylic acid 1-(2-Chloro-4,5-methylenedioxybenzyl)-3-phenyl-5-(3-trifluoromethylbenzyloxy)-indole-2-carboxylic acid 1-(2-Chloro-4,5-methylenedioxybenzyl)-5-(3,4-methylenedioxybenzyloxy)-3-phenylindole-2-carboxylic acid 1-(2-Chloro-4,5-methylenedioxybenzyl)-5-(4-methoxybenzyloxy)-3-phenylindole-2-carboxylic acid 1-(2-Chloro-4,5-methylenedioxybenzyl)-5-cyclohexylmethoxy-3-phenylindole-2-carboxylic acid 1-(2-Chloro-4,5-methylenedioxybenzyl)-3-phenyl-5-(2-trifluoromethylbenzyloxy)-indole-2-carboxylic acid 1-(2-Chloro-4,5-methylenedioxybenzyl)-3-(4-methylphenyl)-5-(4-methylthiobenzyloxy)indole-2-carboxylic acid 1-(2-Chloro-4,5-methylenedioxybenzyl)-3-(3,5-dichlorophenyl)-5-(4-trifluoromethoxybenzyloxy) indole-2-carboxylic acid 1-(2-Chloro-4,5-methylenedioxybenzyl)-5-(2-chloro-4,5-methylenedioxybenzyloxy)-(3-(3,5-dichlorophenyl) indole-2-carboxylic acid 1-(2-Chloro-4,5-methylenedioxybenzyl)-5-(3-furylmethoxy)-3-(4-methylphenyl)-indole-2-carboxylic acid 1-(2-Chloro-4,5-methylenedioxybenzyl)-5-(4-tert-butylbenzyloxy)-3-phenylindole-2-carboxylic acid 1-(2-Chloro-4,5-methylenedioxybenzyl)-5-(3-methoxybenzyloxy)-3-phenylindole-2-carboxylic acid 1-(2-Chloro-4,5-methylenedioxybenzyl)-5-[4-(2,2-dimethylpropanoyl)benzyloxy]-3-phenylindole-2-carboxylic acid 1-(2-Chloro-4,5-methylenedioxybenzyl)-5-(2-methoxybenzyloxy)-3-phenylindole-2-carboxylic acid 1-(2-Chloro-4,5-methylenedioxybenzyl)-5-(4-cyanobutylbenzyloxy)-3-phenylindole-2-carboxylic acid 1-(2-Chloro-4,5-methylenedioxybenzyl)-5-(2-chloro-4,5-methylenedioxybenzyloxy)-3-phenylindole-2-carboxylic acid 1-(2-Chloro-4,5-methylenedioxybenzyl)-5-(4-methylthiobenzyloxy)-3-phenylindole-2-carboxylic acid 5-Benzyloxy-1-(2-chloro-4,5-methylenedioxybenzyl)-3-(4-formylphenyl)-2-carboxylic acid 5-Benzyloxy-1-(2-chloro-4,5-methylenedioxybenzyl)-3-(2-formylphenyl)-2-carboxylic acid 5-Benzyloxy-1-(2-chloro-4,5-methylenedioxybenzyl)-3-(4-fluorophenyl)indole-2-carboxylic acid 3-(3-Aminophenyl)-5-benzyloxy-1-(2-chloro-4,5-methylenedioxybenzyl)indole-2-carboxylic acid; or 5-Benzyloxy-1-(2-chloro-4,5-methylenedioxybenzyl)-3-(2,4-dichlorophenyl)indole-2-carboxylic acid.

* * * * *